United States Patent [19]

Kreczmer

[11] Patent Number: 5,068,420

[45] Date of Patent: Nov. 26, 1991

[54] PROCESS FOR PREPARING ETHER CARBOXYLATE BUILDERS

[75] Inventor: Martin A. Kreczmer, St. Peters, Mo.

[73] Assignee: Monsanto Company, St. Louis, Mo.

[21] Appl. No.: 608,613

[22] Filed: Nov. 9, 1990

Related U.S. Application Data

[63] Continuation-in-part of Ser. No. 458,008, Dec. 28, 1989.

[51] Int. Cl.$^5$ ............................................. C07C 59/245
[52] U.S. Cl. ............................................................ 562/583
[58] Field of Search .......................................... 562/583

[56] References Cited

U.S. PATENT DOCUMENTS

| Re. 30,755 | 9/1981 | Lindsay et al. | 562/583 |
| T101,805 | 5/1982 | Lamberti | 562/583 |
| 3,692,685 | 9/1972 | Lamberti et al. | 562/583 |
| 3,704,320 | 11/1972 | Lannert | 562/583 |
| 3,824,279 | 7/1974 | Lamberti | 562/583 |
| 4,011,264 | 3/1977 | House | 562/583 |
| 4,014,930 | 3/1977 | Feiler et al. | 562/583 |
| 4,243,820 | 1/1981 | Lamberti | 562/580 |
| 4,663,071 | 5/1987 | Bush et al. | 252/174 |
| 4,959,496 | 9/1990 | Crutchfield | 562/583 |

FOREIGN PATENT DOCUMENTS 0320213 6/1989 European Pat. Off. .

OTHER PUBLICATIONS

"Static Mixers and Their Application" Manfred H. Parks et al., International Chemical Engineering, Apr. 1982, vol. 22, No. 2, pp. 197–205.

"In-Line Dispersion and Mass Transfer Using Static Mixing Equipment" F. Streiff, Sulzer Tech. Rev. 3/19/77, pp. 108–113.

*Primary Examiner*—Paul J. Killos

[57] ABSTRACT

There is disclosed a method for purifying the product of a calcium catalyzed reaction, in alkaline reaction medium of salts of maleic acid a hydroxy acid wherein impurities are removed by single stage solvent extraction and separation of the raffinate.

15 Claims, 1 Drawing Sheet

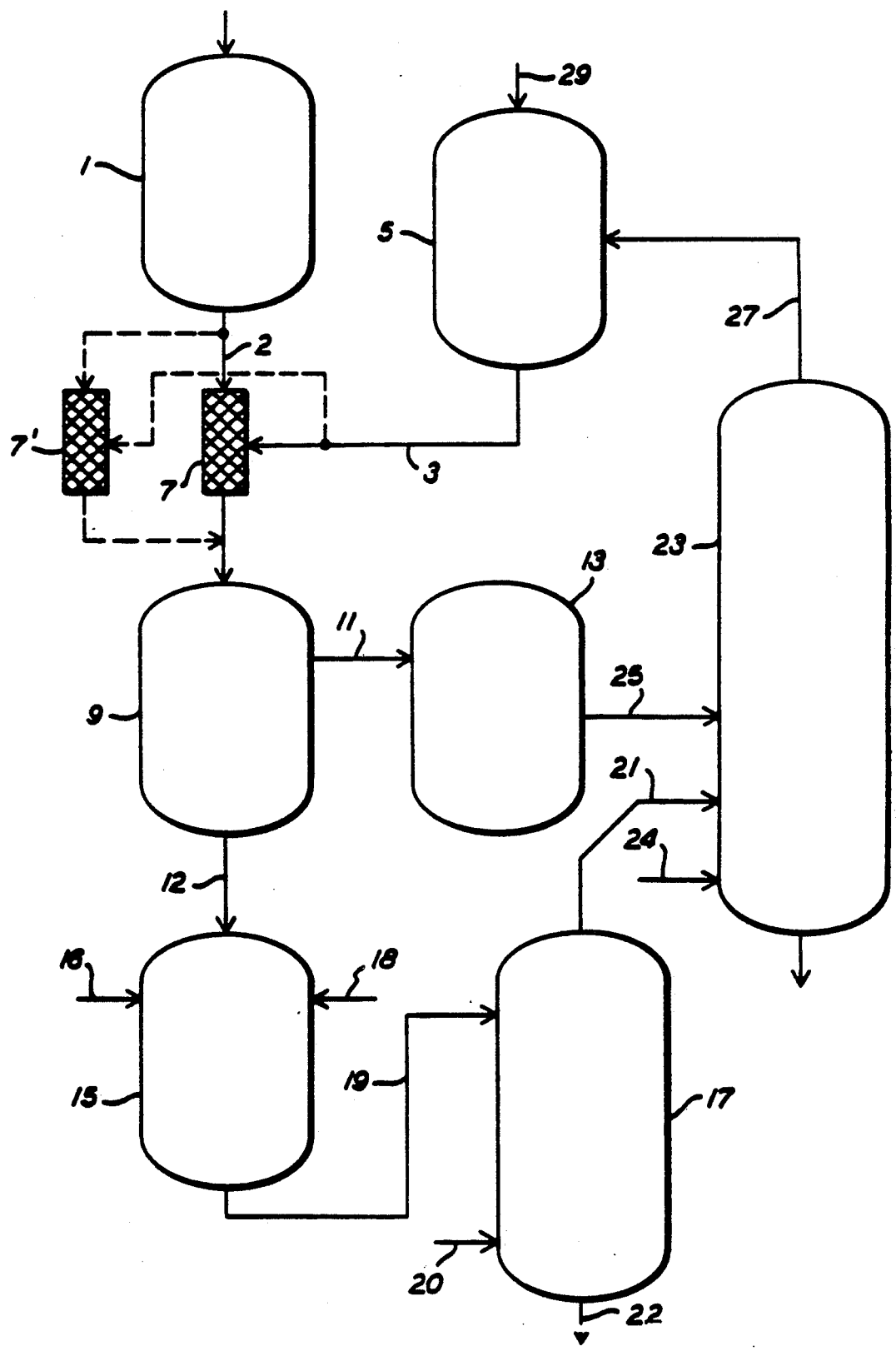

PROCESS FOR PREPARING ETHER CARBOXYLATE BUILDERS

This application is a continuation-in-part application of application Ser. No. 07/458,008 filed Dec. 28, 1989.

This invention relates to a process for making ether carboxylic acids and more particularly to processes for making ether carboxylates prepared by a calcium ion catalyzed reaction in alkaline medium of maleic acid salt and a carboxylate salt containing a reactive hydroxyl group. Such reactions are of the type typically referred to as Michael condensation reactions.

Polycarboxylic acids have long been known to be useful, usually in the salt form, as detergent builders or sequestrants. Also, ether carboxylates useful as metal sequestering and detergent builders have been known and are most desirable for their beneficial effects in laundering applications.

While many carboxylate compounds in the prior art have utility as a builder or sequestrant in laundry detergent formulations, it has been found that certain ether carboxylates are more attractive and cost effective for such utility. In the field of detergent builders and sequestrants for laundry detergent formulations low cost of the components is extremely important because it is in a very competitive market. While many ether carboxylate compounds have been found to be useful there is needed more economical manufacturing processes whereby such compounds can be economically produced in large volume.

One example of ether carboxylates is a mixture of polycarboxylic acids or salts thereof, particularly the sodium salts, of 1-hydroxy-3-oxa-1,2,4,5-pentane tetracarboxylic acid (HOPTC) and 3,6-dioxa-1,2,4,5,7,8-octane hexacarboxylic acid (DOOHC) which is highly useful in detergent formulations as a sequesterant or builder. This mixture is prepared by reaction of a combination of tartrate salts (preferably the D,L-isomer) with maleate salts catalyzed by calcium ions. Due to equilibria present in the reaction and to the need for the presence of particular reactant ratios to obtain particularly preferred ratios of HOPTC and DOOHC in the product, there is considerable unreacted D,L-tartrate and maleate present at the end of the condensation reaction. Further, to provide a more economical process it is desired that a means be found to economically remove impurities from the final product. Such impurities include tartrate, succinate, malate, maleate and fumarate salts.

There has previously been discovered a process for preparing 2,2' oxydisuccinate (ODS) by the reaction of the salts of malic acid and maleic acid, said reaction catalyzed by calcium ions and conducted under alkaline conditions wherein unreacted salts are conveniently recovered in such manner that they may be recycled to the synthesis reaction to produce additional ether carboxylate. It was discovered that at a limited range of acidity certain unreacted salts are conveniently recovered from the reaction mixture at the conclusion of the reaction. By reducing the pH of the reaction mixture to a range within about 4 to about 6 by combining a suitable acid with the reaction mixture, the insoluble salts of starting acids precipitate while the desired ether carboxylate product remains in solution. The precipitate is removed by known means such as filtration thereby allowing further processing of the ether carboxylate solution. Such further processing will depend, of course, upon the particular ether carboxylate produced.

While it is known that removal of impurities can be performed by solvent extraction with methanol, the efficiency of such extraction in large scale production by known methods is too low and large amounts of methanol are required. Reduction of the amount of methanol and the number of extractions would be of great value with respect to efficiency of production of large amounts of product.

While processes are known whereby excellent results are achieved with respect to removal of impurities, such processes also result in excessive loss of product or the use of large amounts of methanol. There is needed an extraction process which achieves the intended purpose of reducing impurities while at the same time providing acceptable product loss and reduced amounts of methanol.

SUMMARY OF THE INVENTION

In one aspect of this invention there is provided an improved process for the purification of the reaction product of a calcium catalyzed reaction of maleic acid and a hydroxy acid in an alkaline reaction medium by means of solvent extraction wherein the extraction can be performed in a manner which achieves both the desired purity of product by means of removal of impurities in the solvent-rich phase and the desired retention of reaction product in the product-rich phase.

In another aspect of this invention there is provided means whereby the reaction product of the above-described reaction is purified by an extraction process with an extractant in a single extraction step followed by a single separation step, preferably by means of gravity.

In yet another aspect of this invention there is achieved a process for purification of mixtures obtained from the calcium catalyzed processes referred to above. The starting mixture for the process of this invention is usually taken from the calcium precipitation step of the manufacturing process wherein the water content of the filtrate is usually in the range of from about 55% to about 62%, by weight of the mixture, although the amount of water at this point is not critical. By the addition of alcohol the amount of water is typically reduced to a range of from about 20% to about 35%, by weight of the mixture and preferably to about 30%, by weight of the mixture. At this amount of water concentration it has been found that the optimum product retention is obtained while at the same time the maximum removal of impurities is also obtained. Less water content causes the raffinate to be too viscous for movement in the process as well requiring more alcohol and higher amounts of water cause excessive solubility losses of the desired product with the extract.

The process of this invention is disclosed in more detail below with respect to exemplary condensation reactions of maleic acid salts and carboxylic or polycarboxylic acid salts containing a reactive hydroxyl group on a non-carbonyl carbon atom. Such reactions provide, for example, mixtures of HOPTC, DOOHC and ODS.

Other typical hydroxy acids include glycolic, mucic, gluconic, isocitric, tartronic and sugar acids such as glucaric and saccharic acids. These acids have in common a reactive hydroxyl group on a non-carbonyl carbon atom.

BRIEF DESCRIPTION OF THE DRAWING

The attached FIG. 1 provides a schematic flow chart whereby one embodiment of this invention may be practiced.

DETAILED DESCRIPTION OF THE INVENTION

The reaction mixture containing ether carboxylate salts is usually processed to remove most of the unreacted starting materials and the calcium catalyst in accordance with known procedures such as are described in U.S. Pat. No. 4,663,071 and EPO 0 320 213. In one embodiment of this invention the unreacted acids are removed by reducing the pH of the reaction mixture to a range of from about 4.5 to about 5.5 by the addition of a suitable acid. The unreacted starting acids precipitate and are removed by conventional means. The calcium catalyst can be then removed by precipitation as described in the above-mentioned patent which is incorporated herein by reference. Again, the precipitate is removed by conventional means and the filtrate from such calcium removal operation is employed in the process of this invention.

The process of this invention will be more clearly understood with reference to the attached FIG. 1 which is intended to be illustrative only and in no way limits the scope of the invention.

In FIG. 1 there is shown a filtrate tank 1 which receives the filtrate from the step of the process whereby calcium carbonate is removed from the reaction product by precipitation. At this point the unreacted starting acids have been removed together with the calcium catalyst leaving the mixture of ether carboxylate salts with minor amounts of impurities which are desirably removed. Such impurities are primarily the salts of maleic, fumaric and formic acid which are in water solution together with the desired product. This filtrate leaves tank 1 through line 2 and is combined with a lower alkyl alcohol through line 3 from alcohol recovery tank 5 in static mixer 7. As noted above, any suitable lower alkyl alcohol having from 1 to about 5 carbon atoms can be employed. For example, ethanol, propanol, butanol, isobutanol or pentanol may be employed, however, methanol is preferred because of its availability and its ability to extract impurities. Methanol has been found to be greatly superior to higher homologs in its ability to extract impurities. For example, on a per pound basis, methanol will extract about twice as much impurities than ethanol. It also follows that ethanol is more efficient than propanol etc.

The alcohol is intimately mixed with the filtrate performed by any suitable means. Such means may include a mixer with suitable blades to mix the alcohol with the filtrate and, in the attached drawing, there is shown the preferred means for intimately mixing the alcohol with the filtrate, said means being static mixer 7. By dashed lines it is shown that the static mixer may be employed in parallel with one or more static mixers such as static mixer 7'. It has been found that adequate mixing of the alcohol into the salt mixture must be performed soon after its addition. Therefore, line 3 is shown entering the feed line to static mixer 7 adjacent or directly into said mixer.

Although blade mixers may be employed, the most preferred embodiments employ a static mixer which has been found to combine efficiency and adaptability to a continuous process. Suitable static mixers having a volume of from about 1 to about 4 liters which are sufficient to provide adequate capacity with acceptable back pressure. The efficiency of mixing at proper water concentration noted below provides for single stage extraction. The volume of the mixer is not critical except for throughput or operating scale. Such static mixers are commercially available and a typical preferred model is sold under the trademark Koch SMV by Koch Engineering Co., Inc, Wichita, Kans. The extraction is desirably maintained at a temperature in the range of about 25° C.

It is most notable that the present process achieves sufficient purity with a single stage extractant employing static mixer 7 followed by a single settling tank 9 wherein the alcohol separates from the raffinate containing the ether carboxylate salts. The extract is removed from the upper portion of settling tank 9 through line 11 to extract feed tank 13. The process of this invention can be employed in batch type as well as continuous operation. The process illustrated in FIG. 1 is the preferred continuous operation which requires that tank sizes be arranged to provide adequate but not too lengthy residence time in settling tank 9. Although residence time may vary broadly it has been found that the time for adequate separation is from about 10 minutes to about 4 hrs. More typically the residence time is from about 30 minutes to about 2 hrs. but should not exceed about six hours. The raffinate, separated from the bottom of extract settling tank 9 is fed through line 12 to a mixing tank 15 wherein the concentration of the carboxylate is adjusted by means of adding water through line 16 and the pH of the mixture is adjusted by means of adding a suitable acid through line 18. The concentration of the ether carboxylate is adjusted so as to be in the range of from about 35% to about 45% and most preferred in the range of from about 41% to about 44%. The pH of the mixture can be adjusted by any suitable acid such as a low molecular weight organic acid as well as a suitable mineral acid. Formic, acetic, propionic or butyric acids are typical examples of low molecular weight organic acids which may be employed while formic acid is preferred. Also, sulfuric acid, nitric acid or hydrochloric acid are typical inorganic acids which may be employed to adjust the pH to the desired level. Other suitable acids may be employed.

After proper dilution and pH adjustment to meet product needs, the raffinate containing the ether carboxylate is fed to a steam stripping column 17 through line 19. Steam is fed to column 17 through line 20 wherein the extractant is removed through the top of the column and the desired, purified product is removed from the bottom of column 17 through line 22. Steam is fed to column 17 through line 20 so as to maintain the column at a temperature when employing methanol, near the top between about 72° C. to about 82° C. and preferably within the range of from about 78° C. to about 80° C. The condensate remains in the product and is considered when adjusting the concentration of the product in mixing tank 15. The extractant alcohol is removed from the top of the column 17 through line 21 to an alcohol recovery column 23. Column 23 is also supplied from the extract feed tank 13 through line 25 to purify the extract obtained from settler 9. Steam is supplied to column 23 through line 24 thereby distilling the alcohol. Normally the column is operated at about 70° C. at the top when methanol is employed. Efficiency of the process is obtained by recovering the alcohol by means of recovery column 23 for recycle in the process of this invention. The steam distilled alcohol is removed from the top of the recovery column 23 through line 27 to the alcohol recovery tank-5.

The purified ether carboxylate salts are provided by removal of the product at the bottom of steam stripping column 17 and waste materials from the extractant are removed from the bottom of recovery column 23 to waste disposal. There is thus seen a cyclical system whereby extractant is efficiently employed in a single stage extraction and recovered from a single stage settler, purified and recycled for reuse. Any loss of extractant alcohol is made up with fresh alcohol through line 29 to alcohol recovery tank 5.

In accordance with this invention it has been found that single stage extraction and separation is achieved when the mixture entering static mixer is in the range of from about 20% to about 35% water by weight. At such concentration of water a wide range of extractant alcohol may be employed. For example, the extractant (100% pure basis) may comprise from about 40% to about 75% by weight of the mixture during the extraction step. Usually from about 46% to about 51% by weight of extractant is sufficient while preferably from about 46% to about 48% by weight is employed. In these ranges of concentration it has been found that selectivity of extraction (the ratio of impurities extracted to product mixture extracted) is most favorable. That is, the most favorable equilibrium is achieved between the impurities to be extracted from the water phase and the impurities concentration in the extractant at such water concentrations.

Water in the filtrate and recovered alcohol is controlled by the way in which the steps producing them are operated. Water concentration in the filtrate is adjusted by varying the temperature at which the calcium precipitation is done. Since this material is concentrated in this step, this temperature fixes the boiling point, and therefore the water (55-62%) left in the filtrate. Water concentration in the alcohol is adjusted by varying the temperature of the recovery column (23) overheads. This sets the dew point on this material, and therefore, the water (5-23%) left in the recovered alcohol. Thus, neither of these streams is adjusted by adding water, but by not removing it. The amounts of water in these two streams together determine the percent water and percent alcohol in the extraction mixture when the streams are mixed.

To demonstrate the above described invention, three batches of 2,2'-oxydisuccinate were prepared according to the process described in the above mentioned EPO 0 320 213. The batches were analyzed before (feed) and after treatment (raffinate) in accordance with invention. Also, the extracts were analyzed. The extraction process was operated with two different amounts of water present in the feed. As will be appreciated, Batch 1 below is employed with an amount of water which is not recommended for use in the process of this invention. The data obtained by these extractions are presented in Table 1 below. Amounts shown in Table 1 are in weight percent. The feed material contained 36.97% 2,2'oxydisuccinate, 2.4% malate, 0.84% maleate, 1.06% fumarate.

TABLE I

|  | FEED | | |
| --- | --- | --- | --- |
|  | 1 | 2 | 3 |
| methanol | 28.6 | 46.4 | 64.3 |
| water | 40.8 | 30.6 | 20.4 |

|  | RAFF. | EXT. | RAFF. | EXT. | RAFF. | EXT. |
| --- | --- | --- | --- | --- | --- | --- |
| ODS | 38.67 | 6.51 | 50.72 | 1.82 | 56.63 | 0.52 |
| malate | 2.26 | 0.86 | 2.87 | 0.40 | 3.23 | 0 |
| maleate | 0.73 | 0.45 | 0.77 | 0.30 | 0.86 | 0.15 |
| fumarate | 0.66 | 1.12 | 0.36 | 0.79 | 0.35 | 0.44 |
| Total impurities | 3.65 | 2.42 | 3.99 | 1.48 | 4.44 | 0.59 |

The data in Table 1 indicates less than desirable results are obtained in Batch 1 which employed 40% water in the feed material to the extraction process. All of the above data in Table 1 was obtained by a single pass extraction process.

The above description illustrates the principle of this invention. The invention is explained and exemplified in a manner so that it can be readily practiced by those skilled in the art. However, it should be clearly understood that such examples are not intended to limit or otherwise change the scope of the invention defined by the following claims.

I claim:

1. In a process for the purification of ether carboxylate salts produced by the calcium catalyzed reaction, in alkaline reaction medium, of salts of maleic acid and a hydroxy acid, the improvement which comprises:
   a. adjusting the pH of the mixture to a range of from about 9 to about 10.5;
   b. providing a water concentration in the mixture of from about 20% to about 35% by weight of the mixture;
   c. extracting impurities from the mixture by intimately contacting the mixture with a lower alkyl alcohol in a single stage, whereby the water content during extraction is in the range of from about 20% to about 35%, by weight; and
   d. separating the alcohol from the mixture.

2. The process of claim 1 wherein step c is performed in a static mixer.

3. The process of claim 1 wherein the water concentration is in the range of from about 55% to about 62%, by weight of the mixture, prior to the addition of alcohol.

4. The process of claim 1 wherein the alcohol is methanol.

5. The process of claim 1 wherein the raffinate is steam stripped to remove trace amounts of alcohol.

6. The process of claim 1 wherein the mixture is maintained at a temperature of about 25° C. during extraction.

7. The process of claim 1 wherein the process is continuous.

8. The process of claim 7 wherein the water concentration is in the range of from about 28% to about 32%, by weight of the mixture, during extraction step.

9. The process of claim 1 wherein the alcohol concentration is in the range of from about 40% to about 65%, by weight of the mixture during the extraction step.

10. The process of claim 1 wherein the alcohol separated from the impurities removed from the mixture is recycled to step c.

11. The process of claim 8 wherein the alcohol is mixed with said mixture by means of a static mixer.

12. The process of claim 1 wherein the ether carboxylate salt in a mixture of HOPTC and DOOHC alkali metal salts.

13. The process of claim 12 wherein the water concentration is in the range of from about 25% to about 35% by weight in step c.

14. The process of claim 1 wherein the ether caroboxylate salt is an alkali metal salt of 2,2'-oxydisuccinate.

15. The process of claim 14 wherein the water concentration is in the range of from 20% to 30% by weight in step c.

* * * * *